United States Patent
Nozato

(10) Patent No.: US 9,468,375 B2
(45) Date of Patent: Oct. 18, 2016

(54) IMAGING METHOD AND IMAGING APPARATUS

(71) Applicant: CANON KABUSHIKI KAISHA, Tokyo (JP)

(72) Inventor: Koji Nozato, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 176 days.

(21) Appl. No.: 13/854,328

(22) Filed: Apr. 1, 2013

(65) Prior Publication Data

US 2013/0265546 A1  Oct. 10, 2013

(30) Foreign Application Priority Data

Apr. 6, 2012 (JP) .................. 2012-087488

(51) Int. Cl.
*A61B 3/14* (2006.01)
*A61B 3/00* (2006.01)
*A61B 3/10* (2006.01)

(52) U.S. Cl.
CPC ...................... *A61B 3/14* (2013.01)

(58) Field of Classification Search
CPC .......... A61B 3/14; A61B 3/12; A61B 3/103; A61B 3/113; A61B 3/1225; A61H 5/00
USPC ........ 351/206, 200, 205, 203, 210, 211, 221
See application file for complete search history.

(56) References Cited

U.S. PATENT DOCUMENTS

| | | | |
|---|---|---|---|
| 8,204,300 B2 | 6/2012 | Sugita et al. | |
| 8,384,908 B2 | 2/2013 | Sugita et al. | |
| 2003/0081174 A1* | 5/2003 | Ross et al. | 351/212 |
| 2011/0116042 A1 | 5/2011 | Nozato | |
| 2012/0019780 A1 | 1/2012 | Nozato | |
| 2012/0062842 A1* | 3/2012 | Griggio et al. | 351/221 |
| 2012/0154746 A1 | 6/2012 | Nozato | |
| 2013/0201448 A1 | 8/2013 | Nozato | |

FOREIGN PATENT DOCUMENTS

JP    2011-104125 A    6/2011

OTHER PUBLICATIONS

Zhang, Y., et al., "High-speed volumetric imaging of cone photoreceptors with adaptive optics spectral-domain optical coherence tomography", Optics Express, vol. 14, No. 10, May 2006, pp. 4380-4394.

* cited by examiner

*Primary Examiner* — Dawayne A Pinkney
(74) *Attorney, Agent, or Firm* — Fitzpatrick, Cella, Harper & Scinto

(57) ABSTRACT

To promptly take a high quality image of an object to be inspected, provided is an imaging method for taking an image of the object to be inspected by irradiating the object to be inspected with measuring light, in which an aberration generated in the object to be inspected is corrected by an aberration correction unit. The method includes the repeatedly performed steps of measuring the aberration generated in the object to be inspected, correcting the aberration by controlling the aberration correction unit in accordance with the measured aberration, and storing, in a storage unit, a control state of the aberration correction unit in association with the measured aberration. The aberration correction unit is controlled in a predetermined control state stored in the storage unit.

25 Claims, 6 Drawing Sheets

IMAGING METHOD AND IMAGING APPARATUS

BACKGROUND OF THE INVENTION

1. Field of the Invention

The present invention relates to an imaging method and an imaging apparatus.

2. Description of the Related Art

In recent years, as an imaging apparatus for ophthalmic application, a scanning laser ophthalmoscope (SLO) and an imaging apparatus employing interference of low coherent light have been developed. The SLO two-dimensionally irradiates a fundus with laser light and receives the reflected light. The imaging apparatus employing the interference of the low coherent light is called an optical coherence tomography (OCT), which is used, in particular, to obtain a tomographic image of the fundus or a vicinity of the fundus. A type of the OCT includes a time domain OCT (TD-OCT) and a spectral domain OCT (SD-OCT), and OCTs using various methods have been being developed.

In particular, in recent years, there has been a progress in achieving an even higher resolution owing to a development of a high numerical aperture (NA) of the irradiation laser in the above-mentioned imaging apparatus for the ophthalmic application. However, when taking an image of a fundus, the image is taken through optical textures of an eye, such as a cornea and a lens. Therefore, as the resolution is increased, the quality of the taken image has become influenced significantly by aberrations of the cornea and the lens.

In order to cope with this problem, researches on an adaptive optics (AO)-SLO and an AO-OCT have been progressed, in which the aberration of an eye is measured and an AO as an adaptive optical system for correcting the aberration is incorporated in an optical system. For example, Document "Y. Zhang et al, Optics Express, Vol. 14, No. 10, 15 May 2006" describes an example of the AO-OCT. In general, the AO-SLO and the AO-OCT measure a wavefront of the eye by using a Shack-Hartmann wavefront sensor system. The Shack-Hartmann wavefront sensor system measures the wavefront of the eye by irradiating the eye with measuring light and receiving the reflected light with a CCD camera through a microlens array. The AO-SLO and the AO-OCT can take a high resolution image by driving a variable shape mirror and a spatial phase modulator to correct the measured wavefront and taking an image of the fundus through the variable shape mirror and the spatial phase modulator.

In an image acquiring apparatus including a general adaptive optical system, a feedback control is performed, in which a process of measuring an aberration of an eye and correcting the aberration based on the measured information is performed repeatedly. The feedback control is performed in order to correct an error generated between an instruction value to a correction device and an actual correction amount, and to respond to fluctuation of an aberration of the eye due to lacrimation or a state of refraction adjustment. Similarly to a general feedback control, the control of aberration correction requires a certain period of time from start of the process until an appropriate aberration correction state is achieved. In particular, because a wavefront sensor or a wavefront correction device used for aberration correction has a low response speed, it takes a few seconds to a few tens of seconds until an appropriate correction state is achieved.

Because a certain period of time is necessary until an appropriate correction state is achieved as described above, a position or state of an object to be inspected changes so that the aberration may be largely changed before an appropriate correction state is achieved, and as a result, the period of time until an appropriate correction state is achieved may be elongated in many cases. For instance, Japanese Patent Application Laid-Open No. 2011-104125 describes a method for reducing the time until an appropriate correction state is achieved by interrupting the control of a correction unit when a position of an eye to be inspected is largely changed.

As described above, there is a case where a state of the eye to be inspected that is not appropriate for imaging may be caused during the feedback control of aberration correction due to a positional change of the eye to be inspected or an influence of eyelash or the like. In this case, because of an influence of the state change, it takes a long time until the aberration is sufficiently reduced, which causes a difficulty in taking an image of the eye to be inspected. In order to take an image of the eye to be inspected, it is preferred that the final aberration be smaller. However, it is possible to take an image thereof when the aberration is corrected to a certain extent. In particular, when the object to be inspected is a human eye, from a viewpoint of mental concentration of a subject or an amount of moisture of the eye, there are many cases where a better result can be obtained by taking an image with a certain extent of correction state rather than by taking a long time to correct sufficiently. However, in the conventional apparatus with an adaptive optical system, it takes a long time until image taking becomes possible, which makes it difficult to take a high quality image of a fundus.

SUMMARY OF THE INVENTION

In view of the above-mentioned problem, the present invention is to provide a method for controlling the adaptive optical system to be an appropriate state in a lapse time when a state of an object to be inspected as an imaging target is changed, and to control the adaptive optical system so that the imaging can be performed soon after the state of the object to be inspected is restored, thereby enabling to promptly take a high quality image.

The present invention provides an imaging method and an imaging apparatus including an adaptive optical system having the following structure.

That is, according to an exemplary embodiment of the present invention, there is provided an imaging method for taking an image of an object to be inspected from reflected light obtained by irradiating the object to be inspected with measuring light, in which an aberration generated in the object to be inspected, when the image is taken, is corrected by an aberration correction unit, the imaging method including the repeatedly performed steps of; measuring the aberration generated in the object to be inspected, correcting the aberration by controlling the aberration correction unit in accordance with the measured aberration; and storing, in a storage unit, a control state when the aberration correction unit corrects the aberration in association with a corresponding aberration, in which the storing is performed when a subsequent aberration measured in the measuring the aberration is equal to or smaller than a prior aberration in time sequence, and the subsequent aberration is corrected by the aberration correction unit in the control state stored in the storage unit when the subsequent aberration is larger than the prior aberration.

Further, according to another exemplary embodiment of the present invention, there is provided an imaging apparatus for taking an image of an object to be inspected from reflected light obtained by irradiating the object to be inspected with measuring light, in which an aberration generated in the object to be inspected is corrected by an aberration correction unit, the imaging apparatus including; an aberration measurement unit for measuring the aberration generated in the object to be inspected, the aberration correction unit for correcting the aberration in accordance with the measured aberration; and a control state storage unit for performing feedback control of the aberration correction unit so as to correct the aberration generated in the object to be inspected based on a measurement result of the aberration measurement unit, and for storing a minimum value of the aberration and a control state of the aberration correction unit when the minimum value is measured during the feedback control.

According to the present invention, it is possible to realize the imaging method and the imaging apparatus that can promptly take the high quality image even when the state of the object to be inspected as the imaging target is changed.

Further features of the present invention will become apparent from the following description of exemplary embodiments with reference to the attached drawings.

BRIEF DESCRIPTION OF THE DRAWINGS

FIG. 4A is a schematic diagram in which the structure is viewed from the lateral side, while FIG. 4B is a schematic diagram illustrating a structure of a state viewed from the direction of plane 4B-4B in FIG. 4A.

FIG. 6A illustrates a state where the wavefront having an aberration enters the sensor, while FIG. 6B illustrates a condensing state on the CCD sensor.

DESCRIPTION OF THE EMBODIMENTS

Modes for carrying out the present invention are described with reference to the following embodiments. However, the present invention is not limited to structures of the following embodiments. Note that, the embodiments describe the case where the object to be inspected is an eye, but the present invention is not limited thereto and can be applied also to other objects to be inspected such as skin and organs as well.

EMBODIMENTS

First Embodiment

As a first embodiment of the present invention, a structure of a fundus imaging apparatus to which the present invention is applied is described with reference to FIG. 1.

In this embodiment, there is described an example where an object to be inspected, which is an object to be measured, is an eye, and an aberration generated at the eye is corrected by an adaptive optical system to take an image of a fundus.

Figure 1:
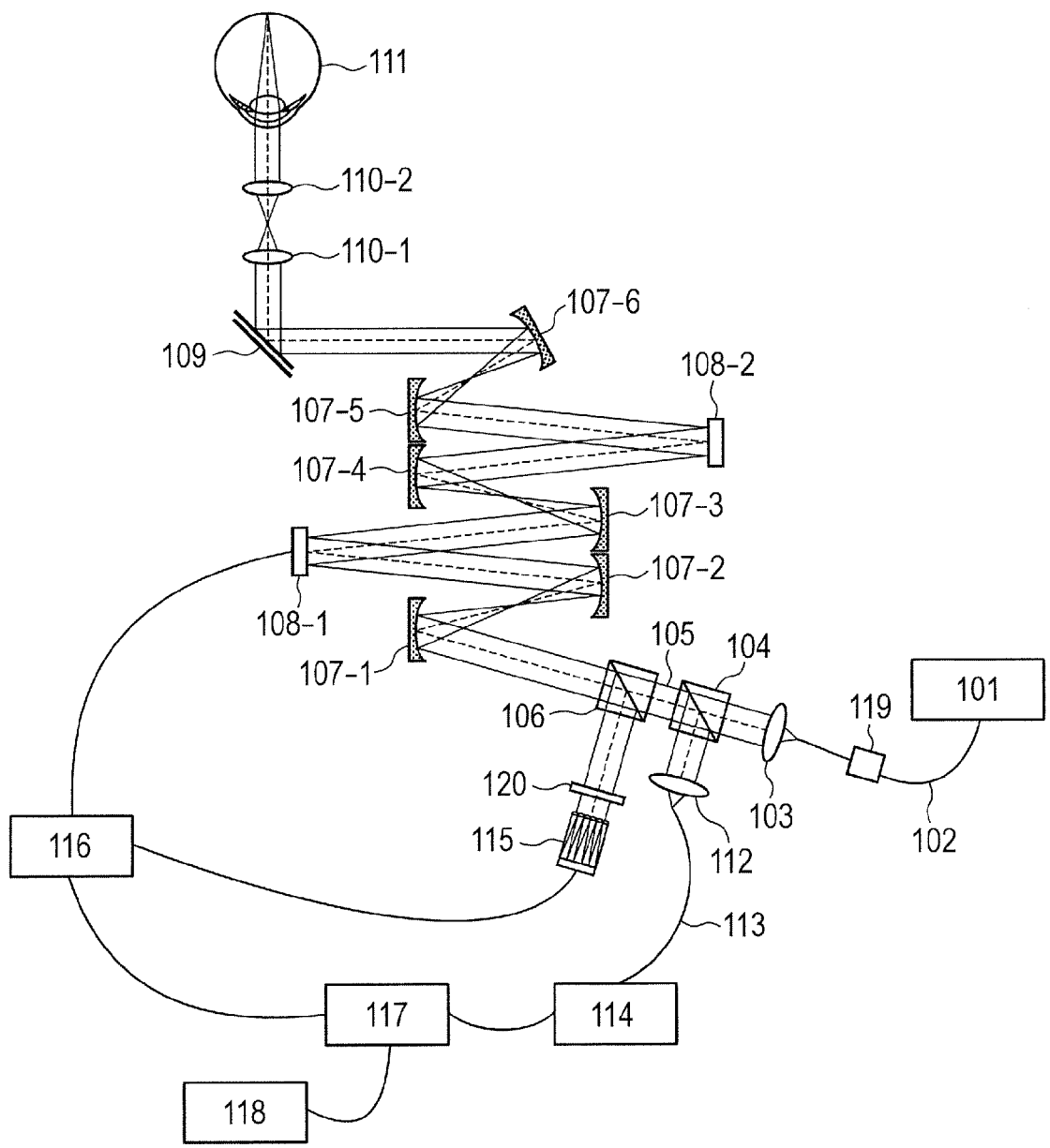
FIG. 1 is a schematic diagram of a structural example of a fundus imaging apparatus corresponding to an SLO including an adaptive optical system according to a first embodiment of the present invention.

In FIG. 1, a light source 101 is a super luminescent diode (SLD) light source having a wavelength of 840 nm. The wavelength of the light source 101 is not particularly limited, but the wavelength of the light source 101 for taking a fundus image is suitably set in a range of approximately 800 nm to 1,500 nm in order to reduce glare for a person to be inspected and maintain a resolution. In this embodiment, the SLD light source is used. In addition to such a light source, for example, a laser light source may be used. In this embodiment, the light source is used in common for taking a fundus image and wavefront measurement, but a structure may be employed in which respective light sources are provided separately and light beams therefrom are superimposed on each other on an optical path.

Light emitted from the light source 101 passes through a single-mode optical fiber 102, and is radiated as collimated light (measuring light 105) by a collimator 103. The polarization of the irradiated light is adjusted by a polarization adjusting member 119 provided on a path of the single-mode optical fiber 102. Another configuration may arrange an optical component for adjusting the polarization on an optical path after the collimator 103. In this embodiment, the polarization adjusting member 119 is adjusted so that the polarized light exiting from the collimator 103 becomes a polarization component parallel to the drawing sheet of FIG. 1. Alternatively, the polarization adjusting unit may not be provided so as not to limit the polarization.

The measuring light 105 radiated from the collimator 103 passes through a light division portion 104 including a beam splitter and then enters an adaptive optical system (aberration correction optical system).

The adaptive optical system includes a light division portion 106, a wavefront sensor 115, wavefront correction devices 108-1 and 108-2, and reflective mirrors 107-1 to 107-6 for guiding the measuring light 105 to those components.

In this case, the reflective mirrors 107-1 to 107-6 are provided so that at least a pupil of an eye 111, the wavefront sensor 115, and the wavefront correction devices 108-1 and 108-2 are in an optically conjugate relationship. In this embodiment, a beam splitter is used as the light division portion 106.

The measuring light 105 passing through the light division portion 106 is reflected on the reflective mirrors 107-1 and 107-2 to enter the wavefront correction device 108-1. The measuring light 105 reflected on the wavefront correction device 108-1 is further reflected on the reflective mirrors 107-3 and 107-4 to enter the wavefront correction device 108-2, thereby traveling to the reflective mirror 107-5.

Figure 2:
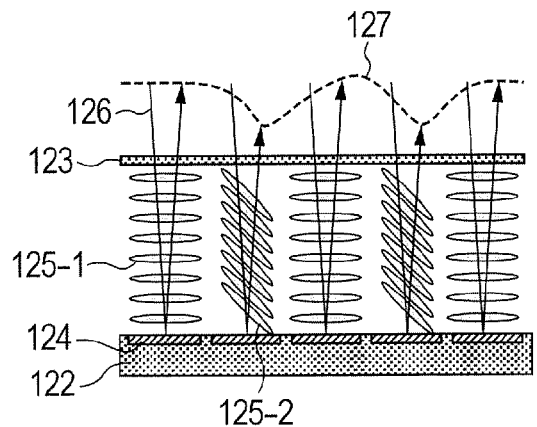
FIG. 2 is a schematic diagram illustrating an example of a wavefront correction device according to the first embodiment of the present invention.

In this embodiment, a spatial phase modulator including a liquid crystal element is used as each of the wavefront correction devices 108-1 and 108-2 serving as an aberration correction unit. FIG. 2 is a schematic diagram of a reflection-type liquid crystal light modulator. This modulator includes a base portion 122, a cover 123, and liquid crystal molecules 125 encapsulated in a space sandwiched by the base portion 122 and the cover 123. The base portion 122 includes multiple pixel electrodes 124. The cover 123 includes a transparent counter electrode (not shown). When no voltages are applied between the pixel electrodes and the counter electrode, the liquid crystal molecules are in such an orientation state as liquid crystal molecules 125-1. When voltages are applied, the orientation state is changed to such an orientation state as liquid crystal molecules 125-2, and hence a refractive index with respect to incident light changes. When a voltage is controlled for each of the pixel electrodes to change a refractive index of each pixel, spatial phase modulation may be realized. For example, when incident light 126 enters the modulator, light passing through the liquid crystal molecules 125-2 is delayed in phase from light passing through the liquid crystal molecules 125-1, to thereby form a wavefront 127 as illustrated in FIG. 2. The reflection-type liquid crystal light modulator generally includes several ten thousand to several hundred thousand pixels.

The liquid crystal light modulator described above mainly modulates light of a specific polarization component. Therefore, in this embodiment, two wavefront correction devices 108-1 and 108-2 are employed to modulate both polarization components, in which the modulating polarization components are substantially orthogonal to each other. The wavefront correction device 108-1 modulates a first polarization component, and the wavefront correction device 108-2 modulates a second polarization component that is orthogonal to the first polarization component.

As another example of the wavefront correction device 108, there is a variable shape mirror. The variable shape mirror is a mirror that can locally change a light reflection direction, and various types thereof are commercialized.

Figure 3:
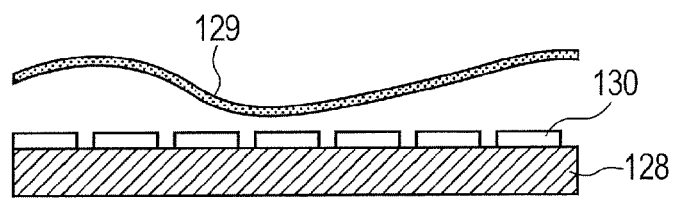
FIG. 3 is a schematic diagram illustrating an example of the wavefront correction device.

For instance, there is a wavefront correction device having a cross-sectional structure as illustrated in FIG. 3. The wavefront correction device includes a film-like mirror surface 129 having a variable shape for reflecting incident light, a base portion 128, actuators 130 disposed to be sandwiched between the film-like mirror surface 129 and the base portion 128, and a support portion (not shown) for supporting the mirror surface 129 at the periphery. As an operating principle of the actuator 130, an electrostatic force, a magnetic force, or a piezoelectric effect may be utilized. Depending on the operating principle, the actuator 130 has a different structure. A plurality of the actuators 130 are two-dimensionally arranged on the base portion 128, and the mirror surface 129 can be arbitrarily deformed by selectively driving the actuators 130. In general, the variable shape mirror includes a few tens to a few hundreds of actuators.

In FIG. 1, the light reflected on the reflective mirrors 107-5 and 107-6 is one-dimensionally or two-dimensionally scanned by a scanning optical system 109. In this embodiment, two galvano-scanners are used as the scanning optical system 109 for main scanning direction (lateral direction of fundus) and sub scanning direction (longitudinal direction of fundus). In order to take an image at a higher speed, a resonance scanner may be used for the scanning optical system 109 for main scanning direction. In order to bring the respective scanners included in the scanning optical system 109 into an optically conjugate relationship, optical elements such as a mirror and a lens may be used between the respective scanners depending on an apparatus structure.

The measuring light 105 scanned by the scanning optical system 109 is radiated to the eye 111 through eyepieces 110-1 and 110-2. The measuring light radiated to the eye 111 is reflected or scattered on the fundus. When the eyepieces 110-1 and 110-2 are adjusted in position, suitable irradiation may be performed in accordance with the diopter of the eye 111. Lenses are used for the eyepiece portion in this embodiment, but, for example, spherical mirrors may be used.

Reflected light which is produced by reflection or scattering on a retina of the eye 111 travels in the reverse direction on the same path as in the case of incidence. A part of the reflected light is reflected by the light division portion 106 toward the wavefront sensor 115 to be used for measuring a light beam wavefront.

Figure 4A:
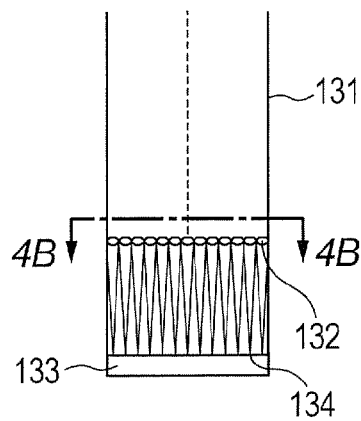
FIGS. 4A and 4B are schematic diagrams illustrating a structure of a Shack-Hartmann sensor.
Figure 4B:
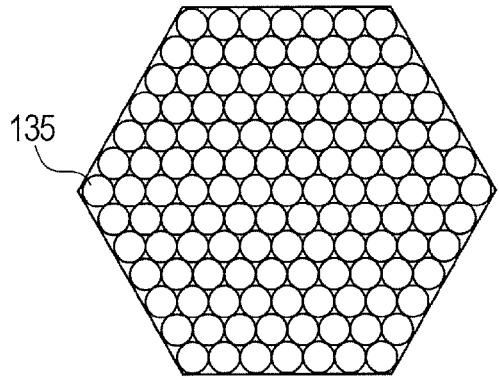
Figure 5:
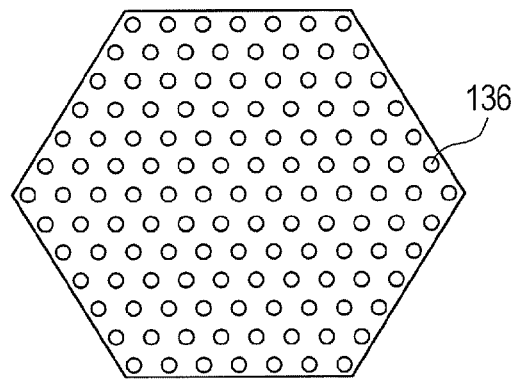
FIG. 5 is a schematic diagram illustrating a state where a light beam for measuring a wavefront is condensed on a CCD sensor.
Figure 6A:
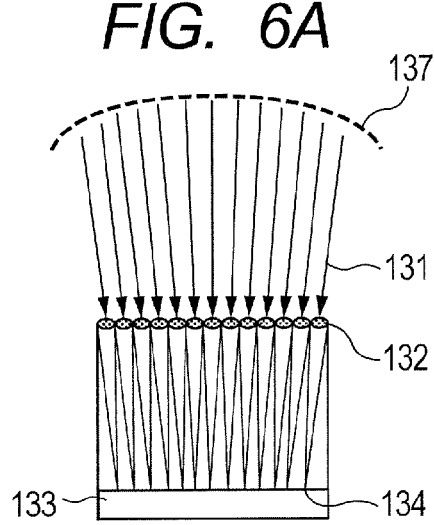
FIGS. 6A and 6B are schematic diagrams illustrating a case where a wavefront having a spherical aberration is measured.
Figure 6B:
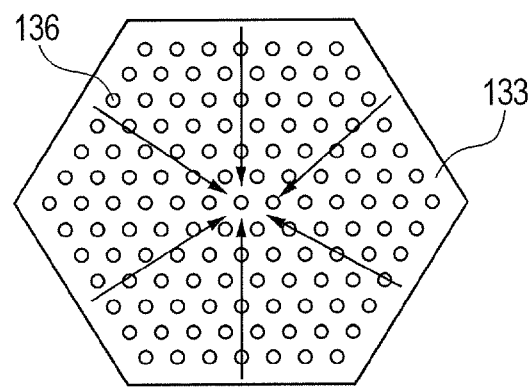

In this embodiment, a Shack-Hartmann sensor is used as the wavefront sensor 115. FIGS. 4A and 4B are schematic diagrams illustrating the Shack-Hartmann sensor. A light beam 131 for wavefront measurement is condensed on a condensing surface 134 of a CCD sensor 133 through a micro-lens array 132. FIG. 4B illustrates a state as viewed from a position indicated by 4B-4B in FIG. 4A, and illustrates a state in which the micro-lens array 132 includes multiple micro-lenses 135. The light beam 131 is condensed on the CCD sensor 133 through the respective micro-lenses 135, and hence the light beam 131 is divided into spots equal in number to the micro-lenses 135 to form the spots. FIG. 5 illustrates a state in which the spots are formed on the CCD sensor 133. The light beam passing through the respective micro-lenses 135 is condensed to form spots 136. A wavefront of the incident light beam is calculated based on the positions of the respective spots 136. For example, FIGS. 6A and 6B are schematic diagrams illustrating a case where a wavefront having a spherical aberration is measured. The light beam 131 is formed to have a wavefront 137. The light beam 131 is condensed at positions in a direction of the local normal to the wavefront by the micro-lens array 132. A condensing state on the CCD sensor 133 in this case is illustrated in FIG. 6B. The light beam 131 has a spherical aberration, and hence the formed spots 136 are biased to the central portion. When the positions of the formed spots 136 are calculated, the wavefront of the light beam 131 may be determined. In this embodiment, the Shack-Hartmann sensor is used as the wavefront sensor. However, the present invention is not limited to this sensor. Another wavefront measurement unit, for example, a curvature sensor may be employed or a method of obtaining the wavefront by reverse calculation from the formed spot images may be employed.

A polarization plate 120 is arranged in front of the wavefront sensor 115 so that only a specific polarization component among the reflected light from the eye enters the wavefront sensor 115. In this embodiment, the polarized light having a wavefront to be measured is limited by the polarization plate 120, but the polarization plate 120 may not be provided so as not to limit the polarization.

The wavefront sensor 115 is connected to an adaptive optics control unit 116. The received wavefront is transferred to the adaptive optics control unit 116. The wavefront correction devices 108-1 and 108-2 are also connected to the adaptive optics control unit 116 and perform modulation instructed from the adaptive optics control unit 116. The adaptive optics control unit 116 calculates a modulation amount (correction amount) for correction of the reflected light to obtain a wavefront having no aberration based on the wavefront obtained by a measuring result of the wavefront sensor 115, and instructs the wavefront correction devices 108-1 and 108-2 to perform the modulation in accordance with the modulation amount. The wavefront measurement and the instruction to the wavefront correction device are repeated and feedback control is performed to always obtain a suitable wavefront.

In FIG. 1, a part of the reflected light passing through the light division portion 106 is reflected by the light division portion 104 and guided to a light intensity sensor 114 via a collimator 112 and an optical fiber 113. The light intensity sensor 114 converts the light into an electric signal, which is used by a control unit 117 for forming a fundus image to be displayed on a display 118.

Figure 7:
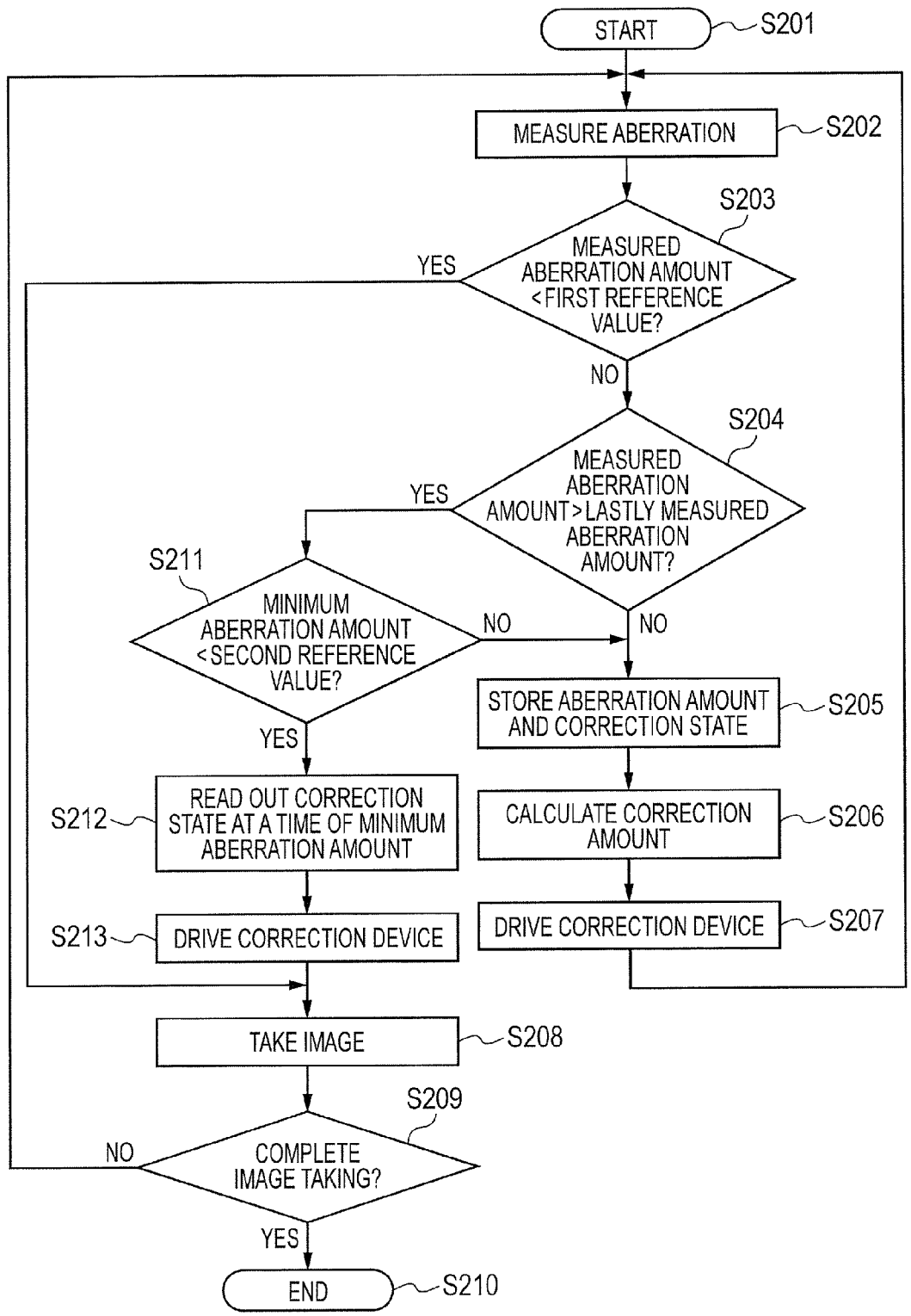
FIG. 7 is a flowchart illustrating control steps of the fundus imaging apparatus according to the first embodiment of the present invention.

Next, control in this embodiment is described with reference to FIG. 7.

The control is started in Step S201. The following steps are performed repeatedly. In Step S202, the wavefront sensor 115 measures an aberration. Based on the measurement result, in Step S206, the adaptive optics control unit 116 calculates a correction amount, and in Step S207, the correction device 108 is driven based on control by the adaptive optics control unit 116.

More specifically, in Step S202 as an aberration measurement step, an aberration of the reflected light is measured so that an aberration amount is determined. In Step S203, the adaptive optics control unit 116 checks whether or not the determined aberration amount is smaller than a preset first reference value or a first threshold value of the aberration amount. Here, the first reference value is a low aberration amount such that a high quality image can be taken, for example. Note that, the first reference value can be an arbitrary value without limiting to the low aberration amount such that a high quality image can be taken.

When it is determined that the measured aberration amount is larger than the reference value of the aberration amount, the processes of Step S204 and subsequent steps are performed. On the other hand, when it is determined that the measured aberration amount is smaller than the reference value of the aberration amount, the control proceeds to Step S208.

When the control proceeds to Step S208, an image is taken in Step S208, and in Step S209, it is determined whether taking the image is completed. When there is no request for completing taking the image, the control goes back to Step S202, adaptive optics processing of Step S202 and subsequent steps is performed again, and the image is taken in Step S208. When there is a request for completing taking the image in Step S209, the control is ended in Step S210.

In Step S204, the measured aberration amount is compared with a lastly measured aberration amount. When the measured aberration amount is smaller than the lastly measured aberration amount, it is considered that the aberration correction feedback is normally working, and hence the control proceeds to Step S205 and the subsequent steps. Note that, in the comparison with the lastly measured aberration amount described above, it is possible to multiply the measured value by a predetermined coefficient so as to be a slightly larger value, and to determine whether or not the feedback operation is normally working with reference to the value obtained by the multiplication.

In Step S205, the measured aberration amount and a control state of the correction device 108 at that time are stored as a set in a memory in the control unit 117. In other words, in Step S205, the wavefront correction device 108 as an aberration correction unit associates the control state when the aberration is corrected with the aberration when the control is performed, and stores them in the memory as a storage unit. Step S205 corresponds to a storing step in the present invention. Based on the measurement result, in Step S206, the adaptive optics control unit 116 calculates the correction amount, and in Step S207, the correction device 108 is driven based on the control by the adaptive optics control unit 116. In other words, Step S207 corresponds to an aberration correction step in the present invention in which the aberration correction device 108 is controlled to perform the aberration correction in accordance with the measured aberration amount. Then, the control goes back to Step S202, and the series of steps are repeated. This operation, in which the control state of the aberration correction device 108 is changed to the control state corresponding to a predetermined condition stored in the memory, is performed in a module region that functions as a changing unit for changing the control state in the control unit 117.

When it is determined in Step S204 that the measured aberration amount is larger than the lastly measured aberration amount, and in particular when a large increase of aberration such as twice of the lastly measured aberration amount or larger is detected, an influence of face movement or eyelash, or a change of state of the eyelid or the like can be considered. In this case, when the feedback process of the aberration correction is continued, it takes a long time until the convergence because of the abnormal state of the object. In addition, even when the aberration amount is converged, it is difficult to take a high quality image because the eye to be inspected is in the incorrect state.

Therefore, when it is determined in Step S204 that the measured aberration amount is larger than the lastly measured aberration amount, for example, the control proceeds to Step S211. In Step S211, the aberration amounts stored in Step S205 are checked, and it is determined whether or not the minimum aberration amount among them is smaller than a preset second reference value of an aberration amount. When the minimum aberration amount is larger than the second reference value, the aberration correction process is insufficient. Therefore, the control proceeds to Step S205, and the feedback process of the aberration correction is further repeated. When the minimum value of the aberration is smaller than the second reference value (second threshold value), the control proceeds to Step S212 so as to read out the control state of the correction device 108 stored as a set with the minimum aberration amount. Then, in Step S213, the correction device 108 is driven so as to be the read out control state. In other words, when the measured aberration amount is smaller than the aberration amount stored in the memory, the aberration amount and the control state of the correction device 108 corresponding to the aberration amount are stored. In this case, the memory functions as a control state storage unit for storing the minimum value of the aberration amount and the control state of the aberration correction device 108 corresponding to the aberration amount when the feedback control of the aberration correction device 108 is performed.

In other words, in the imaging method according to the present invention, the process is repeatedly performed, which includes the aberration measurement step of measuring an aberration generated in the object to be inspected, the aberration correction step of correcting the aberration by controlling the aberration correction unit in accordance with the measured aberration amount, and the storing step of storing, in the storage unit, the control state when the aberration correction unit corrects the aberration in association with the corresponding aberration amount. In this case, in the time sequence, when a subsequent aberration amount measured in the aberration measurement step is equal to or smaller than a prior aberration amount, the storing step is performed. When the subsequent aberration amount is larger than the prior aberration amount, the aberration correction unit performs the correction of the subsequent aberration amount in the control state stored in the storage unit.

In addition, the correction device 108 is driven so as to be the control state read in Step S213, and the image is taken after the object is restored.

The above-mentioned case specified in Step S204 or S211 corresponds to the case where the aberration is relevant to the predetermined condition in the present invention. Because the correction device 108 is fixed in this state, it is sufficiently possible to take a high quality image when the object is restored to a state when the aberration becomes the minimum value. Therefore, in this embodiment, it is regarded that the case where the measured aberration is reduced to be equal to or smaller than the preset second reference value corresponds to the case where the aberration is relevant to the predetermined condition. In this case, an image of the eye to be inspected as the object or the object to be inspected is taken.

In this way, after it is once determined that the measured aberration amount is reduced or smaller than the lastly measured aberration amount, when it is determined in the next measurement that the aberration amount is larger than the lastly measured aberration amount, that is, when the aberration amount is relevant to the predetermined condition in the present invention, the aberration correction device 108 is controlled in the predetermined control state stored in the memory. In this case, the predetermined control state corresponds to the control state when the measured aberration amount becomes the minimum value.

Note that, it is possible to adopt a structure in which, in order to confirm that the state of the object is restored, a monitor for observing an appearance of the eye, for example, is disposed so that an operator can check the appearance of the eye. In this case, the memory may store the state of the object in association with the measured aberration amount. Note that, it is possible to perform matching between the state of the object associated to the aberration (for example, an image of the eye) and an image of the eye that is being observed, and to automatically take the image when a matching degree is equal to or higher than a predetermined value. When the matching degree is equal to or higher than the predetermined value, it is possible to display a message such as "Matching degree is equal to or higher than a predetermined value, so take the image" so as to urge an examiner to take the image. In addition, it is possible to adopt a structure in which a ratio of the current aberration amount, namely the measured aberration amount to the minimum value of the measured aberration amounts or the stored aberration amounts is displayed on a monitor so that the ratio can be checked. Further, it is possible to display a difference between the above-mentioned stored state of the object and the state of the object when the image is taken.

Next, the control proceeds to Step S208 so as to take the image. It is checked in Step S209 whether or not the image taking is completed, and the control is ended in Step S210.

Note that, in Step S204, the aberration correction device 108 is controlled so as to be the control state of the minimum value of the aberration when the measured aberration amount is larger than the lastly measured aberration amount, but this is not a limitation. For instance, it is possible to control the aberration correction device 108 so as to be the control state of the minimum value of the aberration amount when a large increase of the aberration amount such as n times (for example, n=2) or more than the lastly measured aberration amount is detected. In addition, it is possible to display an icon button for instructing to change the control state on the monitor, and to control the aberration correction device 108 so as to be the control state of the minimum value of the aberration amount when this button is operated by the operator. In other words, it is possible to control the aberration correction device 108 in the control state of the minimum aberration as the preset predetermined control state based on the instruction to take the image or the instruction to change the state from the operator.

In this way, according to this embodiment, when the state of the object is significantly changed, the aberration correction is controlled in the optimal state at that time point. Thus, it is possible to promptly take the image when the state of the object is restored, and thus imaging time can be reduced. Note that, it is possible to check, in Step S211, the aberration amounts stored in Step S205, and to determine whether or not there is an aberration smaller than the preset second reference value of the aberration amount other than the minimum aberration amount among the stored aberration amounts. When there is an aberration amount smaller than the preset second reference value, the control state of the correction device 108 stored as a set with the aberration amount is read. Then, the correction device 108 is driven so as to be the control state read in Step S213. Also in this case, it is possible to obtain the effect of reducing the imaging time. In other words, it is sufficient that the aberration amount handled in Steps S211 to S213 be the aberration amount smaller than the second reference value and is not limited to the minimum aberration amount among the aberration amounts stored in Step S205.

Second Embodiment

Figure 8:
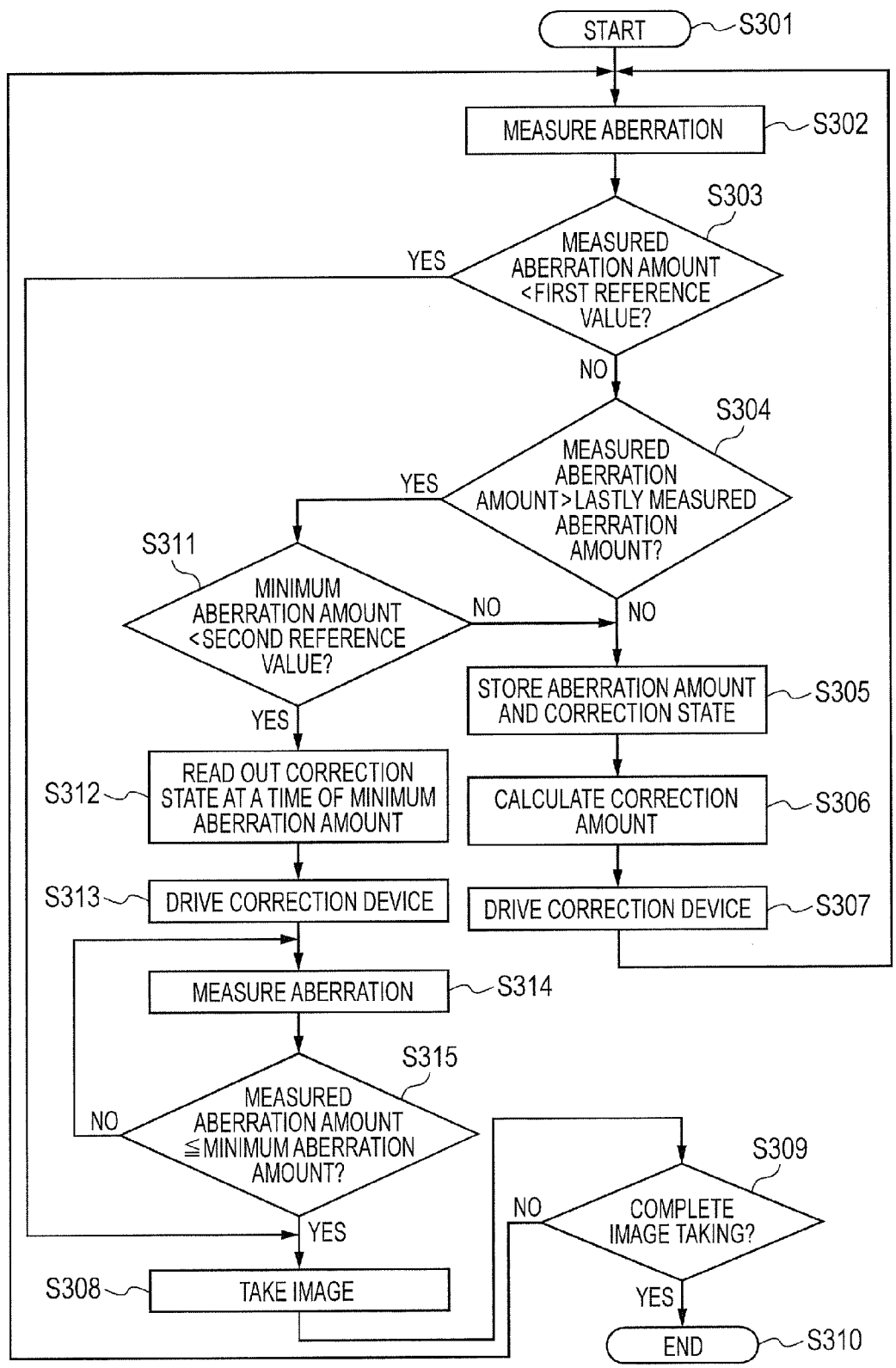
FIG. 8 is a flowchart illustrating control steps of a fundus imaging apparatus according to a second embodiment of the present invention.

As a second embodiment of the present invention, an example of a control method of the fundus imaging apparatus having a form different from that in the first embodiment to which the present invention is applied is described with reference to a flowchart of FIG. 8. In this embodiment, the basic apparatus structure is the same as that of the first embodiment. There is disposed an anterior eye observing portion for observing a state of the eye 111, and a state of the anterior eye part is displayed on the monitor.

The control is started in Step S301. The following steps are performed repeatedly. In Step S302, the wavefront sensor 115 measures an aberration. Based on the measurement result, in Step S306, the adaptive optics control unit 116 calculates a correction amount, and in Step S307, the correction device 108 is driven based on control by the adaptive optics control unit 116.

More specifically, in Step S302, an aberration of the reflected light is measured so that an aberration amount is determined. In Step S303, the adaptive optics control unit 116 checks whether or not the determined aberration amount is smaller than a preset first reference value of the aberration amount. In this case, the first reference value is a low aberration amount such that a high quality image can be taken, for example. Note that, the first reference value can be an arbitrary value without limiting to the low aberration amount such that a high quality image can be taken.

When it is determined that the aberration amount is larger than the first reference value, the processes of Step S304 and subsequent steps are performed. On the other hand, when it is determined that the aberration amount is smaller than the first reference value, the control proceeds to Step S308.

When the control proceeds to Step S308, an image is taken in Step S308, and in Step S309, it is determined whether taking the image is completed. When there is no request for completing taking the image, the control goes back to Step S302, adaptive optics processing of Step S302 and subsequent steps is performed again, and the image is taken in Step S308. When there is a request for completing taking the image in Step S309, the control is ended in Step S310.

In Step S304, the measured aberration amount is compared with the lastly measured aberration amount. When the measured aberration amount is smaller than the lastly measured aberration amount, it is considered that the aberration correction feedback is normally working, and hence the control proceeds to Step S305 and the subsequent steps. Note that, in the comparison with the lastly measured aberration amount described above, it is possible to multiply the measured value by a predetermined coefficient so as to be a slightly larger value, and to determine whether or not the feedback operation is normally working with reference to the value obtained by the multiplication.

In Step S305, the measured aberration amount and a control state of the correction device 108 at that time are stored as a set in the memory in the control unit 117. Based on the measurement result, in Step S306, the adaptive optics control unit 116 calculates the correction amount, and in Step S307, the correction device 108 is driven based on the control by the adaptive optics control unit 116. Then, the control goes back to Step S302, and the series of steps are repeated.

For instance, when it is determined in Step S304 that the measured aberration amount is increased to be larger than the lastly measured aberration amount, the control proceeds to Step S311. Note that, similarly to Step S204, it is possible to control the aberration correction device 108 so as to be the control state of the minimum value of the aberration amount when a large increase of the aberration amount such as n times (for example, n=2) or more than the lastly measured aberration amount is detected. In Step S311, the aberration amounts stored in the memory are checked, and it is determined whether or not the minimum aberration amount among them is smaller than the preset second reference value of the aberration amount. When the minimum aberration amount is larger than the second reference value, the aberration correction process is insufficient. Therefore, the control proceeds to Step S305, and the feedback process of the aberration correction is further repeated. When the minimum value of the aberration amount is smaller than the second reference value, the control proceeds to Step S312 so as to read out the control state of the correction device 108 stored as a set with the minimum aberration amount. Then, in Step S313, the correction device 108 is driven so as to be the read out control state. Because the correction device 108 is fixed to this state, it is sufficiently possible to take a high quality image when the object is restored to the state when the aberration becomes the minimum value.

In order to confirm that the state of the object is restored, in Step S314, the aberration is measured, and in Step S315, the measured aberration amount is compared with the minimum aberration amount. When the measured aberration amount is larger than the minimum aberration amount, it is considered that the state of the object is not restored yet. Therefore, the control goes back to Step S314. When the measured aberration amount is equal to or smaller than the minimum aberration amount, it is considered that the state of the object is restored. Therefore, the control proceeds to Step S308, and the imaging and following steps are performed. In this case, while Step S314 or S315 is being performed, it is desired to perform works such as adjusting a position of the eye and opening the eyelid simultaneously.

By performing this process, after completion of the aberration correction feedback, efficiency of restoring the state of the object to the optimal state is improved, and it becomes possible to promptly take a high quality image.

Third Embodiment

Figure 9:
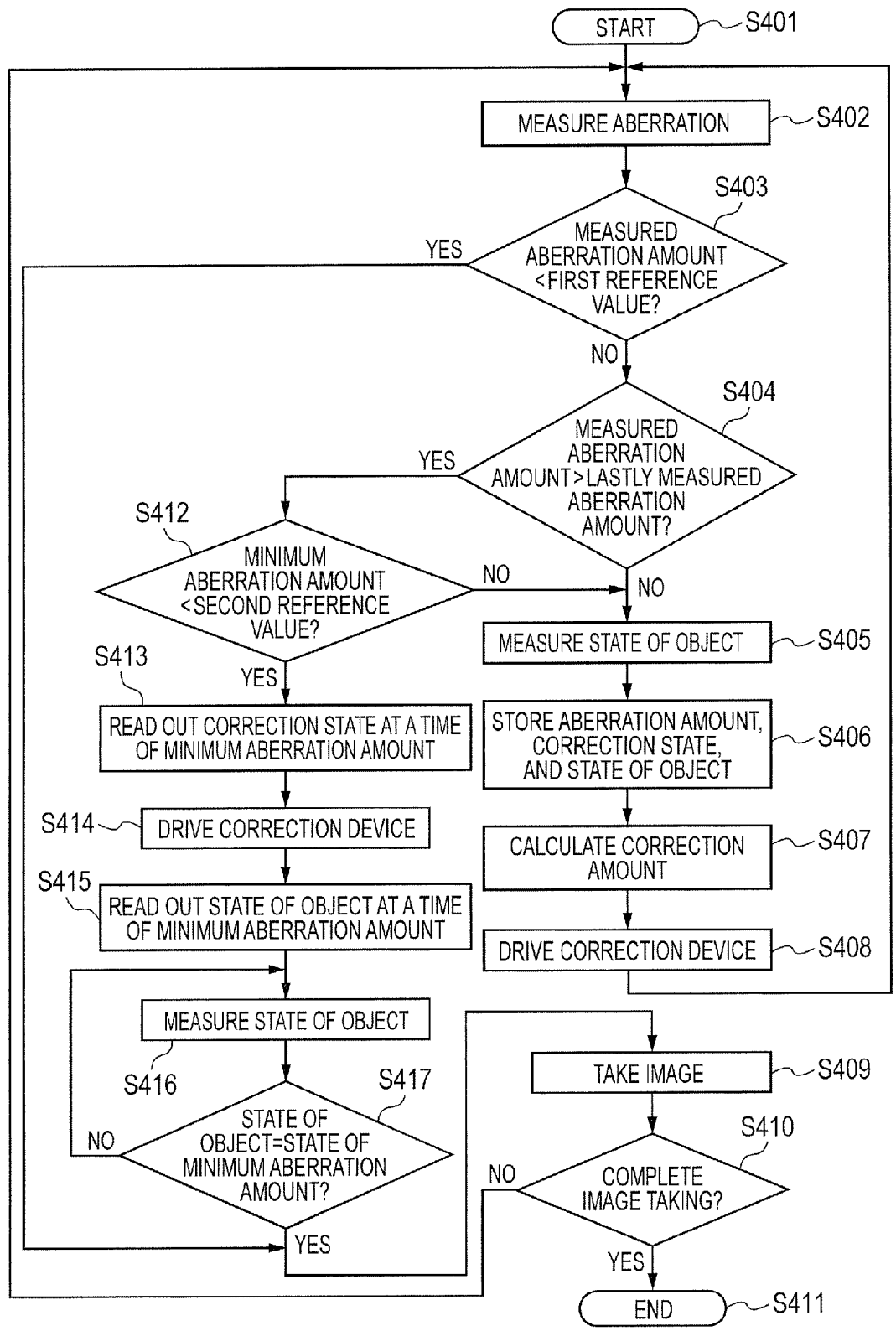
FIG. 9 is a flowchart illustrating control steps of a fundus imaging apparatus according to a third embodiment of the present invention.

As a third embodiment of the present invention, an example of a control method of the fundus imaging apparatus having a form different from that of the first embodiment to which the present invention is applied is described with reference to a flowchart of FIG. 9. In this embodiment, the basic apparatus structure is the same as that of the first embodiment.

The control is started in Step S401. The following steps are performed repeatedly. In Step S402, the wavefront sensor 115 measures an aberration. Based on the measurement result, in Step S407, the adaptive optics control unit 116 calculates a correction amount, and in Step S408, the correction device 108 is driven based on control by the adaptive optics control unit 116.

More specifically, in Step S402, an aberration is measured so that an aberration amount is determined. In Step S403, the adaptive optics control unit 116 checks whether or not the determined aberration amount is smaller than a preset first reference value of the aberration amount. In this case, the first reference value is a low aberration amount such that a high quality image can be taken, for example. Note that, the first reference value can be an arbitrary value without limiting to the low aberration amount such that a high quality image can be taken.

When the determined aberration amount is larger than the first reference value, the processes of Step S404 and subsequent steps are performed. On the other hand, when the aberration amount is smaller than the first reference value, the control proceeds to Step S409.

When the control proceeds to Step S409, an image is taken in Step S409, and in Step S410, it is determined whether taking the image is completed. When there is no request for completing taking the image, the control goes back to Step S402, adaptive optics processing of Step S402 and subsequent steps is performed again, and the image is taken in Step S409. When there is a request for completing taking the image in Step S410, the control is ended in Step S411.

In Step S404, the measured aberration amount is compared with the lastly measured aberration amount. When the measured aberration amount is smaller than the lastly measured aberration amount, it is considered that the aberration correction feedback is normally working, and hence the control proceeds to Step S405 and the subsequent steps. Note that, in the comparison with the lastly measured aberration amount described above, it is possible to multiply the measured value by a predetermined coefficient so as to be a slightly larger value, and to determine whether or not the feedback operation is normally working with reference to the value obtained by the multiplication.

In Step S405, the state of the object is measured. The state of the object means a relative position of the object to the apparatus or an observed appearance of the anterior eye part. For instance, in this embodiment, the state of the object corresponds to a position of the pupil of the eye to be inspected. Note that, in this case, the state of the object exemplified as a position of the object or the appearance is stored in a module region that functions as a to-be-inspected object state storage unit in the memory in association with the aberration amount measured when the state is obtained as data. In addition, this state includes a position or location of the object with respect to the imaging apparatus. In this case, when the image of the object is taken, it is preferred to display a difference between the stored state of the object and the state of the object when the image is taken.

In Step S406, the measured aberration amount, the control state of the correction device 108 at that time, and the state of the object are stored as a set in the memory in the control unit 117. Based on the measurement result, in Step S407, the adaptive optics control unit 116 calculates the correction amount, and in Step S408, the correction device 108 is driven based on the control by the adaptive optics control unit 116. Then, the control goes back to Step S402, and the series of steps are repeated.

When it is determined in Step S404 that the measured aberration amount is increased to be larger than the lastly measured aberration amount, the control proceeds to Step S412. Note that, similarly to Step S204, it is possible to control the aberration correction device 108 so as to be the control state of the minimum value of the aberration amount when a large increase of the aberration amount such as n times (for example, n=2) or more than the lastly measured aberration amount is detected. In Step S412, the aberration amounts stored in the memory are checked, and it is determined whether or not the minimum aberration amount among them is smaller than the preset second reference value of the aberration amount. When the minimum aberration amount is larger than the second reference value, the aberration correction process is insufficient. Therefore, the control proceeds to Step S405, and the feedback process of the aberration correction is further repeated. When the minimum value of the aberration amount is smaller than the second reference value, the control proceeds to Step S413 so as to read out the control state of the correction device 108 stored as a set with the minimum aberration amount. Then, in Step S414, the correction device 108 is driven so as to be the read out control state. Because the correction device 108 is fixed to this state, it is sufficiently possible to take a high quality image when the object is restored to the state when the aberration becomes the minimum value.

In Step S415, the state of the object stored as a set with the minimum aberration amount is read. In order to confirm that the state of the object is restored, in Step S416, the state of the object is measured, and in Step S417, the measured state is compared with the state at the minimum value. When the measured state is the same as the state at the minimum value, the control proceeds to Step S409, and the imaging and following steps are performed. In this case, while Step S416 or S417 is performed, it is desired to perform works such as adjusting a position of the eye and opening the eyelid simultaneously.

By performing this process, after completion of the aberration correction feedback, efficiency of restoring the state of the object to the optimal state is improved, and it becomes possible to promptly take a high quality image.

Note that, it is possible to automatically take the image when the comparison result in Step S417 indicates a matching degree which is equal to or higher than a predetermined value or higher. When the matching degree is equal to or higher than a predetermined value, it is possible to display a message such as "Matching degree is equal to or higher than a predetermined value, so take the image" so as to urge an examiner to take the image.

Other Embodiments

Further, the present invention is also realized by performing the following process. Specifically, in this process, software (program) for realizing the functions of the above-mentioned embodiments is supplied to a system or an apparatus via a network or various kinds of storage medium, and a computer (CPU, MPU, or the like) of the system or the apparatus reads out and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-087488, filed Apr. 6, 2012, which is hereby incorporated by reference herein in its entirety.

What is claimed is:

1. An imaging method for taking an image of an object to be inspected from reflected light obtained by irradiating the object to be inspected with measuring light, in which an aberration generated in the object to be inspected, when the image is taken, is corrected by an aberration correction unit, the imaging method comprising the repeatedly performed steps of:
    measuring an amount of the aberration generated in the object to be inspected;
    comparing (a) a prior aberration amount, measured by measuring an amount of the aberration, with (b) a subsequent aberration amount that is subsequent in time sequence;
    storing, in a storage unit, (a) a control state of the aberration correction unit at a time of measuring the amount of the aberration, in association with (b) a corresponding amount of the aberration; and
    correcting the aberration by controlling the aberration correction unit in accordance with the measured amount of the aberration,
    wherein the storing is performed when the subsequent aberration amount is equal to or smaller than the prior aberration amount, and
    wherein the aberration corresponding to the subsequent aberration amount is corrected by the aberration correction unit in the control state stored in the storage unit when the subsequent aberration amount is larger than the prior aberration amount.

2. An imaging method according to claim 1, wherein the measuring step, the correcting step, and the storing step are repeated when the prior aberration amount is larger than a preset first threshold value.

3. An imaging method according to claim 1, wherein the image of the object to be inspected is taken when the subsequent aberration amount is reduced to a preset second threshold value.

4. An imaging method according to claim 1, wherein the image of the object to be inspected is taken when the subsequent aberration amount is equal to or smaller than a minimum aberration amount stored in the storing.

5. An imaging method according to claim 1, further comprising displaying one of (a) the subsequent aberration amount (b) a ratio of the subsequent aberration amount to a minimum value of stored amounts of the aberration.

6. An imaging method according to claim 1, wherein the storing comprises:
   storing a state of the object to be inspected in association with the subsequent aberration amount; and
   displaying, when the image of the object to be inspected is taken, a difference between a state of the object to be inspected when the image is taken and the stored state.

7. An imaging method according to claim 6, wherein the state of the object to be inspected to be stored comprises a position of the object to be inspected.

8. An imaging method according to claim 1, further comprising controlling the aberration correction unit in a predetermined control state based on one of an instruction to take the image and an instruction to change the control state from an operator.

9. An imaging method according to claim 8, further comprising displaying a button for the instruction to change the control state on a display unit.

10. A non-transitory computer-readable medium including a program that when run on a computer causes the execution of the imaging method according to claim 1.

11. An imaging apparatus for taking an image of an object to be inspected from reflected light obtained by irradiating the object to be inspected with measuring light, in which an aberration generated in the object to be inspected, when the image is taken, is corrected by an aberration correction unit, the imaging apparatus comprising:
   an aberration measurement unit for measuring an amount of the aberration generated in the object to be inspected;
   the aberration correction unit for correcting the aberration in accordance with the measured amount of the aberration;
   a comparing unit for comparing (a) a prior aberration amount, measured by measuring an amount of the aberration, with (b) a subsequent aberration amount that is subsequent in time sequence; and
   a control state storage unit for performing feedback control of the aberration correction unit so as to correct the aberration generated in the object to be inspected based on a measurement result of the aberration measurement unit, and for storing a minimum value of the amount of the aberration and a control state of the aberration correction unit when the minimum value is measured during the feedback control based on a comparing result of the comparing unit.

12. An imaging apparatus according to claim 11, further comprising a to-be-inspected object state storage unit for storing a state of the object to be inspected.

13. An imaging apparatus according to claim 12, wherein the to-be-inspected object state storage unit includes a unit for storing an appearance of the object to be inspected.

14. An imaging apparatus according to claim 12, wherein the to-be-inspected object state storage unit includes a unit for storing a position of the object to be inspected.

15. An imaging apparatus for taking an image of an object to be inspected from reflected light obtained by irradiating the object to be inspected with measuring light, in which an aberration generated in the object to be inspected, when the image is taken, is corrected, the imaging apparatus comprising:
   an aberration measurement unit for measuring an amount of the aberration generated in the object to be inspected;
   a comparing unit for comparing (a) a prior aberration amount measured by measuring an amount of the aberration, with (b) a subsequent aberration amount that is subsequent in time sequence;
   an aberration correction unit for correcting the aberration in accordance with the measured amount of the aberration;
   a control state storage unit for storing, in a storage unit, (a) a control state when the aberration correction unit corrects the aberration, in association with (b) a corresponding amount of the aberration; and
   a changing unit for changing the control state of the aberration correction unit to a control state satisfying a predetermined condition stored in the storage unit when the subsequent aberration amount is larger than the prior aberration amount.

16. An imaging method according to claim 1, wherein when the subsequent aberration amount is larger than the prior aberration amount, the storing is not performed.

17. An imaging method according to claim 1, wherein when the subsequent aberration amount is smaller than or equal to the prior aberration amount, the control state used for correcting the subsequent aberration amount by the aberration correction unit is stored in association with the subsequent aberration amount.

18. An imaging method according to claim 1, wherein the object to be inspected is a fundus of an eye.

19. An imaging apparatus according to claim 11, wherein the object to be inspected is a fundus of an eye.

20. An imaging apparatus according to claim 15, wherein the object to be inspected is a fundus of an eye.

21. An imaging apparatus according to claim 15, wherein the control state satisfying the predetermined condition is a control state of the aberration correction unit at a time of measuring the subsequent aberration amount when the subsequent aberration amount is smaller than the prior aberration amount.

22. An imaging apparatus for taking an image of an object to be inspected from reflected light obtained by irradiating the object to be inspected with measuring light, in which an aberration generated in the object to be inspected, when the image is taken, is corrected, the imaging apparatus comprising:
   an aberration measurement unit for measuring an amount of the aberration generated in the object to be inspected;
   a comparing unit for comparing (a) a prior aberration amount measured by measuring an amount of the aberration, with (b) a subsequent aberration amount that is subsequent in time sequence;
   an aberration correction unit for correcting the aberration in accordance with the measured amount of the aberration; and
   a control unit for controlling the aberration correction unit based on a result of the comparing by the comparing unit,
   wherein the control unit stores in a storage unit a correction state corresponding to the subsequent aberration amount and controls the aberration correction unit based on a correction state corresponding to the subsequent aberration amount, when the subsequent aberration amount is equal to or smaller than the prior aberration amount, and
   wherein the control unit reads out from the storage unit a correction state corresponding to the prior aberration amount and controls the aberration correction unit based on the correction state which is read out, corresponding to the prior aberration amount, when the subsequent aberration amount is larger than the prior aberration amount.

23. An imaging apparatus according to claim 22, wherein the control unit makes the aberration correction unit be in the correction state corresponding to the prior aberration amount when the subsequent aberration amount is larger than the prior aberration amount.

24. An imaging method for taking an image of an object to be inspected from reflected light obtained by irradiating the object to be inspected with measuring light, in which an aberration generated in the object to be inspected, when the image is taken, is corrected, the imaging method comprising the steps of:

measuring an amount of the aberration generated in the object to be inspected;

comparing (a) a prior aberration amount measured by measuring an amount of the aberration, with (b) a subsequent aberration amount that is subsequent in time sequence; and correcting the aberration in accordance with (1) the measured amount of the aberration and (2) a result of the comparing, wherein a correction state corresponding to the subsequent aberration amount is stored in a storage unit and the correction is performed based on the correction state corresponding to the subsequent aberration amount, when the subsequent aberration amount is equal to or smaller than the prior aberration amount, and wherein a correction state corresponding to the prior aberration amount is read out from the storage unit and the correction is performed based on the correction state which is read out, corresponding to the prior aberration amount, when the subsequent aberration amount is larger than the prior aberration amount.

25. An imaging method according to claim 24, wherein the correction is performed in the correction state corresponding to the prior aberration amount when the subsequent aberration amount is larger than the prior aberration amount.

* * * * *